(12) United States Patent
Paul

(10) Patent No.: US 12,268,899 B2
(45) Date of Patent: Apr. 8, 2025

(54) RADIATION THERAPY SYSTEM

(71) Applicant: Muir IP Ltd, Cork (IE)

(72) Inventor: Kevin Paul, Lisbon (PT)

(73) Assignee: Muir IP Ltd, Cork (IE)

( * ) Notice: Subject to any disclaimer, the term of this patent is extended or adjusted under 35 U.S.C. 154(b) by 517 days.

(21) Appl. No.: 17/604,486

(22) PCT Filed: Jan. 31, 2020

(86) PCT No.: PCT/EP2020/000031
§ 371 (c)(1),
(2) Date: Oct. 18, 2021

(87) PCT Pub. No.: WO2020/211971
PCT Pub. Date: Oct. 22, 2020

(65) Prior Publication Data
US 2022/0233885 A1 Jul. 28, 2022

(30) Foreign Application Priority Data
Apr. 18, 2019 (GB) ...................................... 1905568

(51) Int. Cl.
*A61N 5/10* (2006.01)
(52) U.S. Cl.
CPC .... *A61N 5/1081* (2013.01); *A61N 2005/1094* (2013.01)
(58) Field of Classification Search
CPC ...... A61N 5/10; A61N 5/1001; A61N 5/1049; A61N 5/1077; A61N 5/1079; A61N 5/1081
See application file for complete search history.

(56) References Cited

U.S. PATENT DOCUMENTS

| 5,321,271 A | 6/1994 | Schonberg |
| 5,349,198 A | 9/1994 | Takanaka |

(Continued)

FOREIGN PATENT DOCUMENTS

| EP | 986071 A2 | 3/2000 |
| EP | 3829709 A1 | 6/2021 |

(Continued)

OTHER PUBLICATIONS

International Search Report and Written Opinion of the ISA from corresponding PCT Application No. PCT/EP2020/000031, dated Apr. 16, 2020.

(Continued)

*Primary Examiner* — David E Smith
(74) *Attorney, Agent, or Firm* — Gardner, Linn, Burkhart & Ondersma LLP

(57) ABSTRACT

A radiation therapy system comprises a treatment pod having an internal treatment room, and a beam delivery system comprising a particle accelerator for generating a radiation beam. The beam delivery system is carried by the treatment pod with the particle accelerator outside of the pod, and is configured to deliver the radiation beam to the treatment room. The beam delivery system, including the accelerator is movable around the treatment pod in order to adjust the position of the radiation beam with respect to the treatment room. The movement of the beam delivery system is counterbalanced. The treatment pod, together with the beam delivery system, may be moved in order to service multiple waiting rooms.

21 Claims, 10 Drawing Sheets

(56) References Cited

U.S. PATENT DOCUMENTS

| | | | |
|---|---|---|---|
| 5,818,058 A | 10/1998 | Nakanishi | |
| 2006/0260050 A1 | 11/2006 | Manzione | |
| 2007/0131876 A1* | 6/2007 | Brahme | A61B 6/4429 |
| | | | 250/492.1 |
| 2011/0101254 A1 | 5/2011 | Yajima | |
| 2013/0035587 A1* | 2/2013 | Lagendijk | A61N 5/1081 |
| | | | 600/411 |
| 2013/0066134 A1* | 3/2013 | Carol | A61N 5/10 |
| | | | 378/65 |
| 2013/0235969 A1 | 9/2013 | Winter et al. | |
| 2015/0087883 A1 | 3/2015 | Boudreau | |
| 2018/0014797 A1 | 1/2018 | Keibel | |
| 2020/0346040 A1 | 11/2020 | Paul | |
| 2021/0299479 A1* | 9/2021 | Hooftman | A61N 5/1081 |

FOREIGN PATENT DOCUMENTS

| | | | |
|---|---|---|---|
| WO | 9415670 A1 | 7/1994 | |
| WO | 2008067893 A1 | 6/2008 | |
| WO | 2013033249 A2 | 3/2013 | |
| WO | 2014132502 A1 | 9/2014 | |
| WO | WO-2015161036 A1 * | 10/2015 | A61B 6/0407 |
| WO | 2019077135 A1 | 4/2019 | |

OTHER PUBLICATIONS

UK Search Report of corresponding Application No. GB1905568.0, dated Oct. 9, 2019.

* cited by examiner

RADIATION THERAPY SYSTEM

CROSS REFERENCE TO RELATED APPLICATION

The present application is a national filing in the US of International Patent Application No. PCT/EP2020/000031, filed Jan. 31, 2020 which claims benefit of Great Britain Patent Application No. 1905568.0, filed Apr. 18, 2019.

FIELD OF THE INVENTION

The present invention relates to radiation therapy systems. The invention relates particularly, but not exclusively, to hadron beam therapy systems.

BACKGROUND TO THE INVENTION

Treatment of cancer and other illnesses using charged particles such as protons and ions is known but is currently prohibitively expensive. The main cost drivers of proton and ion beam therapy are the proton and ion accelerators and beam transport systems, which typically require very large gantries and large, typically multi-storey, buildings. The gantries themselves require high-tech engineering, with low production volume and are therefore expensive. The placement of the treatment rooms, which tend to be spread out over a large area also increases the overall cost. Single treatment room systems have also been proposed, but these are also housed in large buildings with large complex gantries, and are relatively expensive because of the provision for only one treatment room. Particle accelerators can weight in excess of 100 tonnes, which is beyond the lifting capabilities of modern robots, and so the particle accelerators tend to be static during use, the radiation beam being transported to the treatment room by a beam transport system comprising a relatively long beam transport line terminating with a delivery nozzle. The foot print of the building is determined by the length and shape of the beam line feeding the various treatment rooms, and the beam line requires shielding along its entire length. Moreover, the beam lines invariably bend to reach their destination and this complicates the system, increasing its expense and reducing its efficiency. In addition, with conventional treatment systems it is difficult to make efficient use of the radiation equipment given the relatively long times required to set up the equipment for each patient and for organising the patients themselves. Unfortunately therefore the benefits of, in particular, proton therapy have been overshadowed by the relatively high cost of conventional hospital based facilities.

SUMMARY OF THE INVENTION

It would be desirable to provide a radiation therapy system that mitigates at least some of the problems outlined above and makes hadron therapy less expensive than is conventionally achievable.

An aspect of the invention provides a radiation therapy system comprising a treatment pod having an internal treatment room and a beam delivery system comprising a particle accelerator for generating a radiation beam. The beam delivery system is carried by the treatment pod and is configured to deliver the radiation beam to the treatment room. The said beam delivery system is movable with respect to the treatment pod in order to adjust the position of the radiation beam with respect to the treatment room.

The beam delivery system may be moveable, at least partly and optionally fully, around the pod and around the treatment room, preferably in an orbital manner. Said beam delivery system may be rotatable about an axis of said treatment pod, preferably the longitudinal axis of said treatment pod.

The particle accelerator may be located externally of the treatment pod.

In typical embodiments, the beam delivery system includes a beam delivery nozzle, and the beam delivery nozzle is located inside said treatment room.

The treatment pod typically comprises a hollow body structure that defines the treatment room, the beam delivery system being carried by the body structure. Preferably, the beam delivery system is coupled to the treatment pod, conveniently to the body structure, with the particle accelerator located outside of the body structure and the beam delivery nozzle extending through the body structure. The body structure may comprise a solid sleeve-like wall extending around a longitudinal axis of the pod.

In some embodiments, the body structure includes a rotatable section, the beam delivery system being coupled to said rotatable section, and wherein, typically, the body structure includes first and second end sections, said rotatable section being located between and rotatable with respect to said first and second end sections.

Typically, the pod has first and second ends, either one or both of which are open to provide access to the treatment room.

The treatment pod may include a counterbalance, which is preferably located externally of the pod, the counterbalance being arranged to counterbalance movement of the beam delivery system with respect to the treatment pod, the counterbalance preferably being arranged to counterbalance rotational movement of the beam delivery system about a rotation axis, the rotation axis preferably being the longitudinal axis of the pod. The counterbalance is preferably rotatable around the pod together with the beam delivery system, and is preferably oppositely disposed to the beam delivery system with respect to the rotational axis.

The counterbalance may be coupled to the body structure, preferably to a rotatable section of said body structure, and is preferably located outside of the body structure.

Optionally, said counterbalance comprises a second beam delivery system comprising a second particle accelerator for generating a second radiation beam, and being configured to deliver said second radiation beam into said treatment room, said second particle accelerator preferably being located externally of said pod.

In some embodiments, the system includes a plurality of waiting rooms, said treatment pod being aligned with, or movable into alignment with, each of said waiting rooms to allow access to the treatment room from each waiting room. The treatment pod and beam delivery system are movable together as an assembly. Advantageously, the waiting rooms are arranged in at least one pair of oppositely disposed waiting rooms, the respective waiting rooms of the, or each, pair being spaced apart with their respective doorway facing each other, and wherein said treatment pod is locatable between the respective waiting rooms of the, or each, pair to allow access to the treatment room from either of the respective waiting rooms.

In some embodiments, there is a single pair of oppositely disposed waiting rooms, the treatment pod being located between, and aligned with, each waiting room. In other embodiments, there are multiple pairs of oppositely disposed waiting rooms, and wherein said treatment pod is movable into alignment with any one of said pairs of waiting rooms. The multiple pairs of waiting rooms may be arranged to define a common passage between opposing waiting rooms, and wherein said treatment pod is located in and movable along said passage. The multiple pairs of waiting rooms may be arranged in a linear array such that said common passage is linear. The multiple pairs of waiting rooms may be arranged such that said common passage is circular or curvilinear.

In some embodiments, said plurality of waiting rooms are arranged in a linear, circular or curvilinear array, said treatment pod being movable into alignment with any one of said waiting rooms to allow access to the treatment room from each waiting room.

In some embodiments, the system includes conveyancing means for moving said treatment pod into alignment with any one of said waiting rooms, or any two oppositely disposed waiting rooms.

Optionally, said waiting rooms are arranged in multiple storeys, said system including a lift device for moving said treatment pod between said storeys.

In some embodiments, the system includes a bay, or other housing structure, for housing the treatment pod, the treatment pod being supported above a floor of the bay to provide space below the treatment pod to accommodate the particle accelerator as the beam delivery system rotates. The bay typically provides said passage.

In some embodiments, the system further includes a radiation shielding structure that at least partly surrounds the treatment pod and the beam delivery system. The radiation shielding structure may comprise a top shield section located so as to provide radiation shielding above the treatment pod and beam delivery system; first and second side shield sections located so as to provide radiation shielding at opposite sides, respectively, of the treatment pod and the beam delivery system, and first and second end shield sections located so as to provide radiation shielding at opposite ends, respectively, of the treatment pod and the beam delivery system.

The radiation shielding structure may enclose the treatment pod and the beam delivery system at least from above, at opposite sides and at opposite ends.

The radiation shielding structure may comprise at least one doorway aligned with a respective doorway of the treatment pod, each doorway having a respective door formed at least partly from radiation shielding material.

Another aspect the invention provides a system that may be the same or similar to the system of the prior aspect except that the beam delivery system may be any other type of therapy delivery system, not necessarily a particle or hadron therapy system, and therefore not necessarily including a particle accelerator.

From yet another aspect the invention provides a system that may be the same or similar to the system of the prior aspects except that the beam delivery system may be in a fixed location with respect to the pod.

Although embodiments of the invention are described herein in the context of a radiation therapy system having a beam delivery system comprising a particle accelerator for generating a radiation beam, the invention may alternatively be used with other beam delivery systems that do not include a particle accelerator, instead comprising means for generating other types of beam, e.g. an ultrasound beam. Alternatively, the beam delivery system may be replaced by an alternative patient treatment system or patient scanning system, e.g. MRI scanning equipment or CT scanning equipment.

Other advantageous aspects of the invention will be apparent to those ordinarily skilled in the art upon review of the following description of specific embodiments and with reference to the accompanying drawings.

BRIEF DESCRIPTION OF THE DRAWINGS

Embodiments of the invention are now described by way of example and with reference to the accompanying drawings in which like numerals are used to denote like parts and in which.

DETAILED DESCRIPTION OF THE DRAWINGS

Referring now in particular to FIGS. 1 to 5 of the drawings there is shown, generally indicated as 10, a radiation therapy system embodying one aspect of the present invention. The system 10 includes a radiation beam delivery system 12 and may be described as an external beam radiotherapy (EBRT) system. The beam delivery system 12 comprises a particle accelerator 16. The particle accelerator 16 may comprise any suitable conventional particle accelerator, for example a linear accelerator, a cyclotron, a synchro-cyclotron, a synchrotron, or a laser based accelerator, and produces a radiation beam (not illustrated) for use in patient treatments, in particular tumour RT. The radiation beam typically comprises ionizing radiation. The nature of the radiation beam depends on the radiation source (not shown) with which the particle accelerator 16 is used. In preferred embodiments, the radiation source comprises a source of protons. As such the radiation beam comprises a proton beam and the system 10 may be described as a proton therapy system. Alternatively, the radiation source may comprise other suitable particles, especially but not exclusively charged particles, for example ions (e.g. Carbon ions, Helium ions or Neon ions), atoms, photons or other subatomic particles such as electrons, alpha particles, beta particles, negative pi mesons or neutrons, or any particle suitable for use in particle therapy or hadron therapy. Hence, in alternative embodiments the radiation beam may comprise, for example, an ion beam, electron beam (especially a relativistic electron beam), a neutron beam, photon beam gamma-ray beam or X-ray beam. The radiation source may be incorporated into the particle accelerator 16 or connected to it in any convenient conventional manner.

Figure 1:
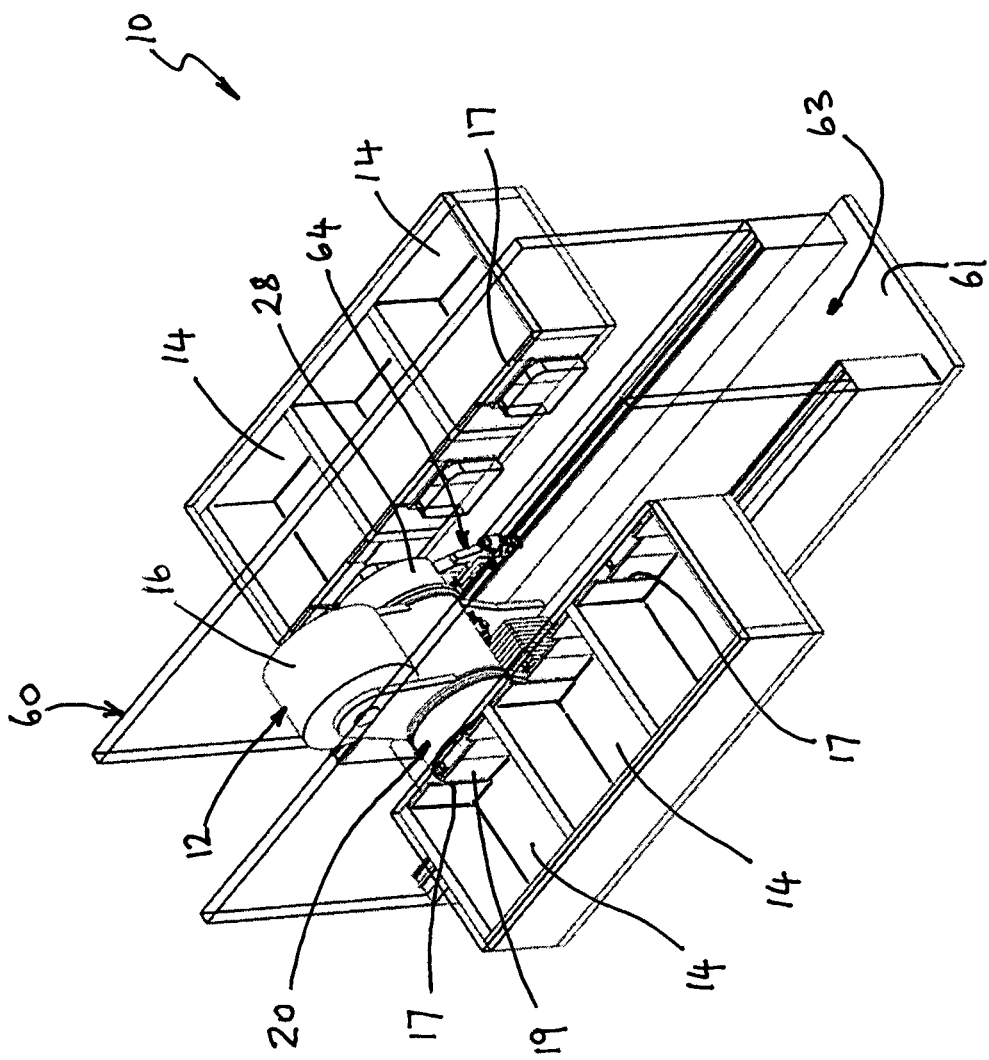
FIG. 1 is a first perspective view of a radiation therapy system embodying one aspect of the present invention, some of the components of the system being shown as transparent in order not to obscure other components from view.
Figure 2:
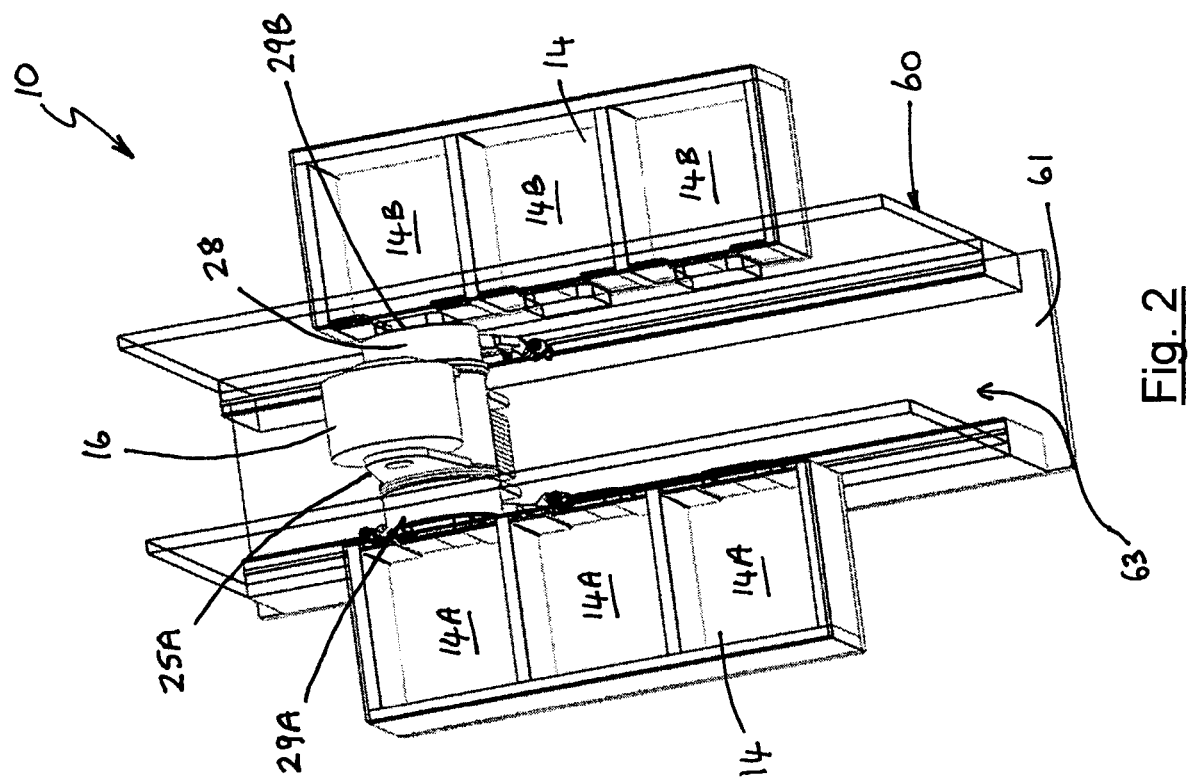
FIG. 2 is a second perspective view of the radiation therapy system of FIG. 1.
Figure 3:
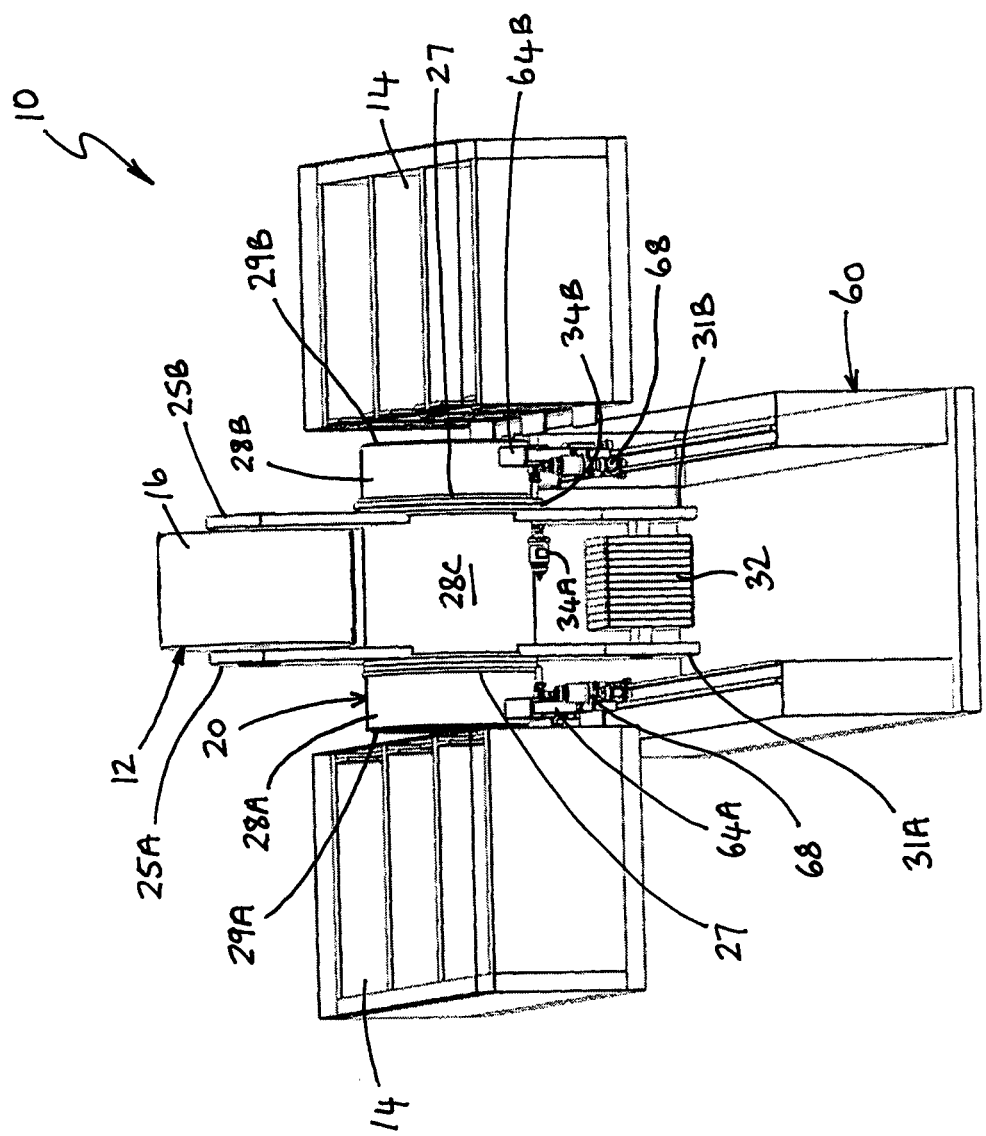
FIG. 3 is a third perspective view of the radiation therapy system of FIG. 1.
Figure 4:
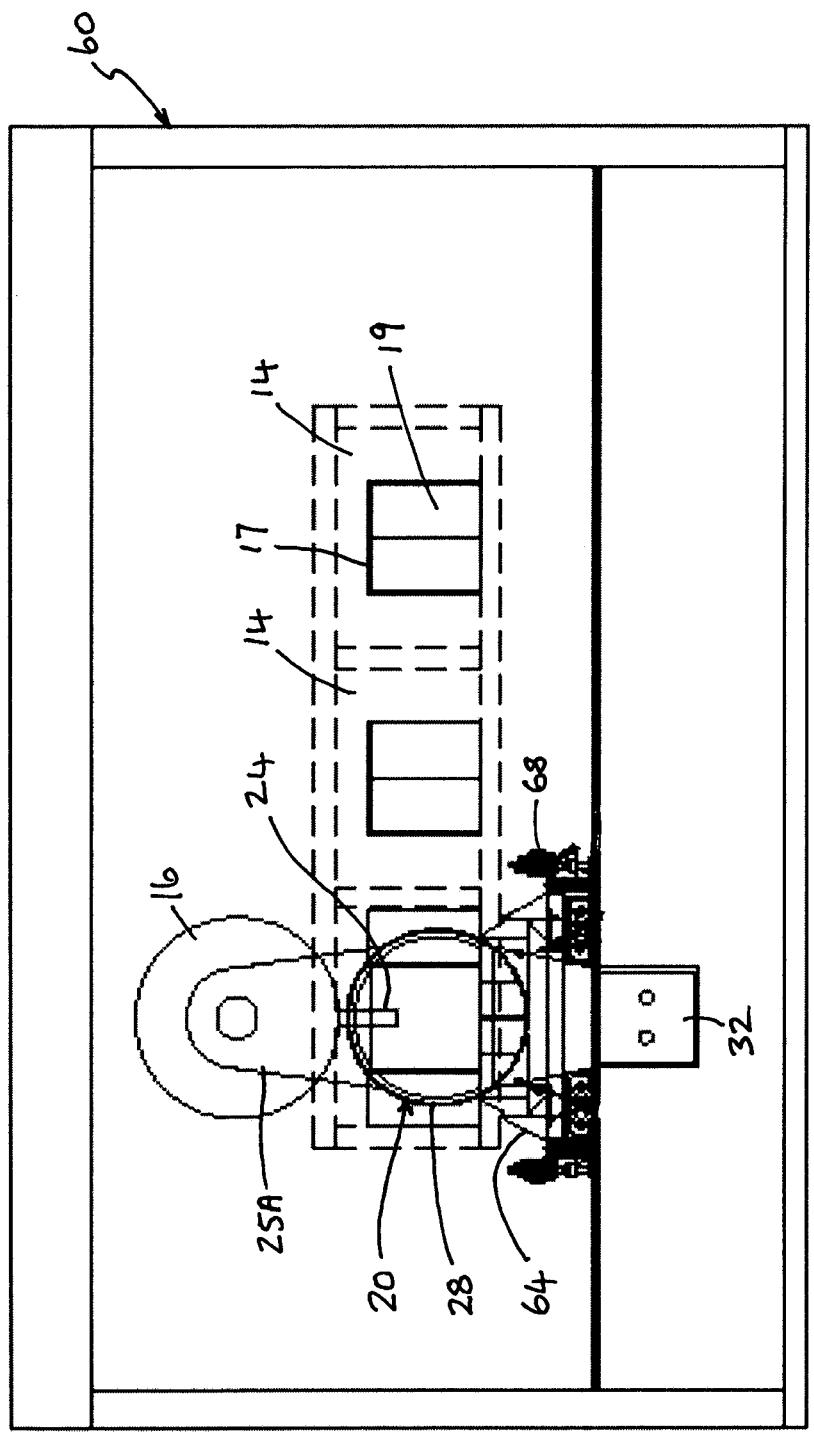
FIG. 4 is a side sectioned view of the radiation therapy system of FIG. 1.
Figure 5:
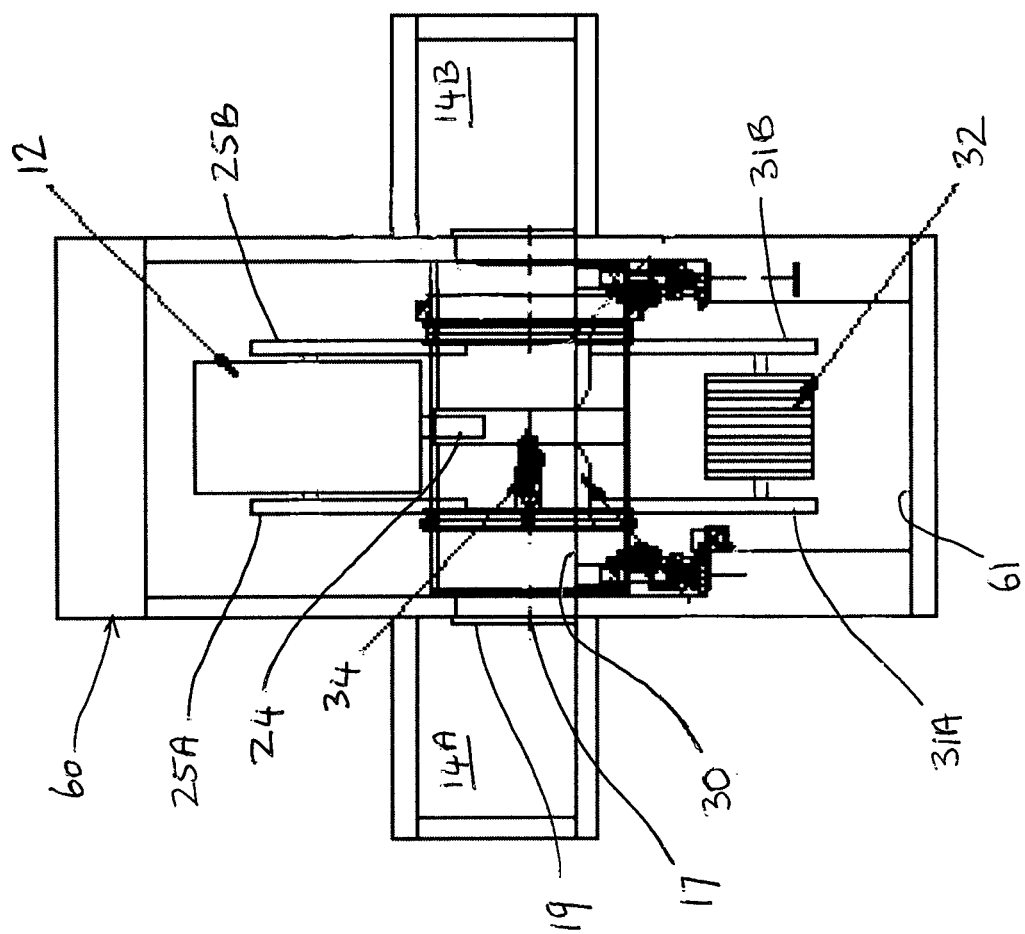
FIG. 5 is an end sectioned view of the radiation therapy system of FIG. 1.
Figure 6:
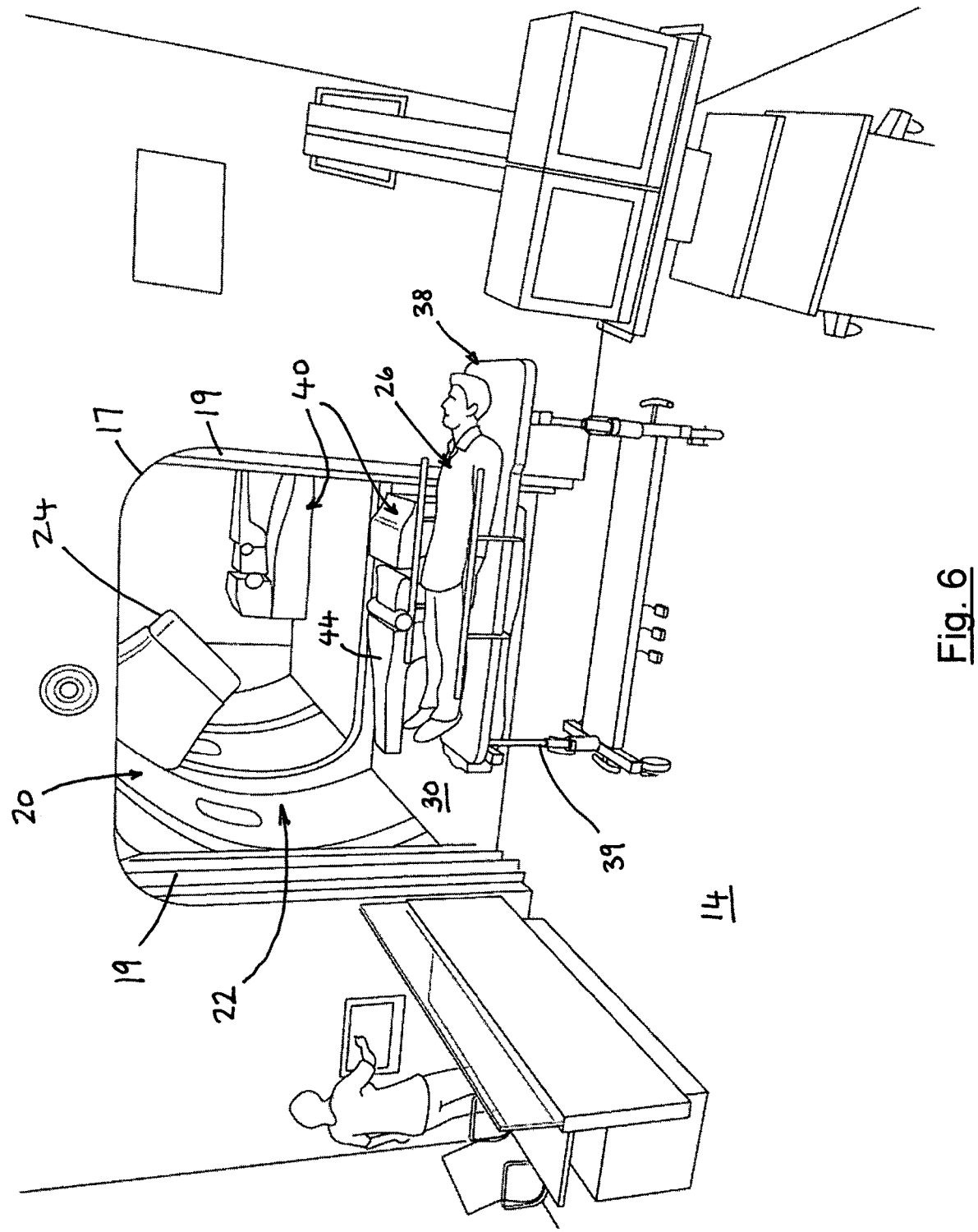
FIG. 6 is a first view of a waiting room and a treatment room, each room being part of the radiation therapy system of FIG. 1.
Figure 7:
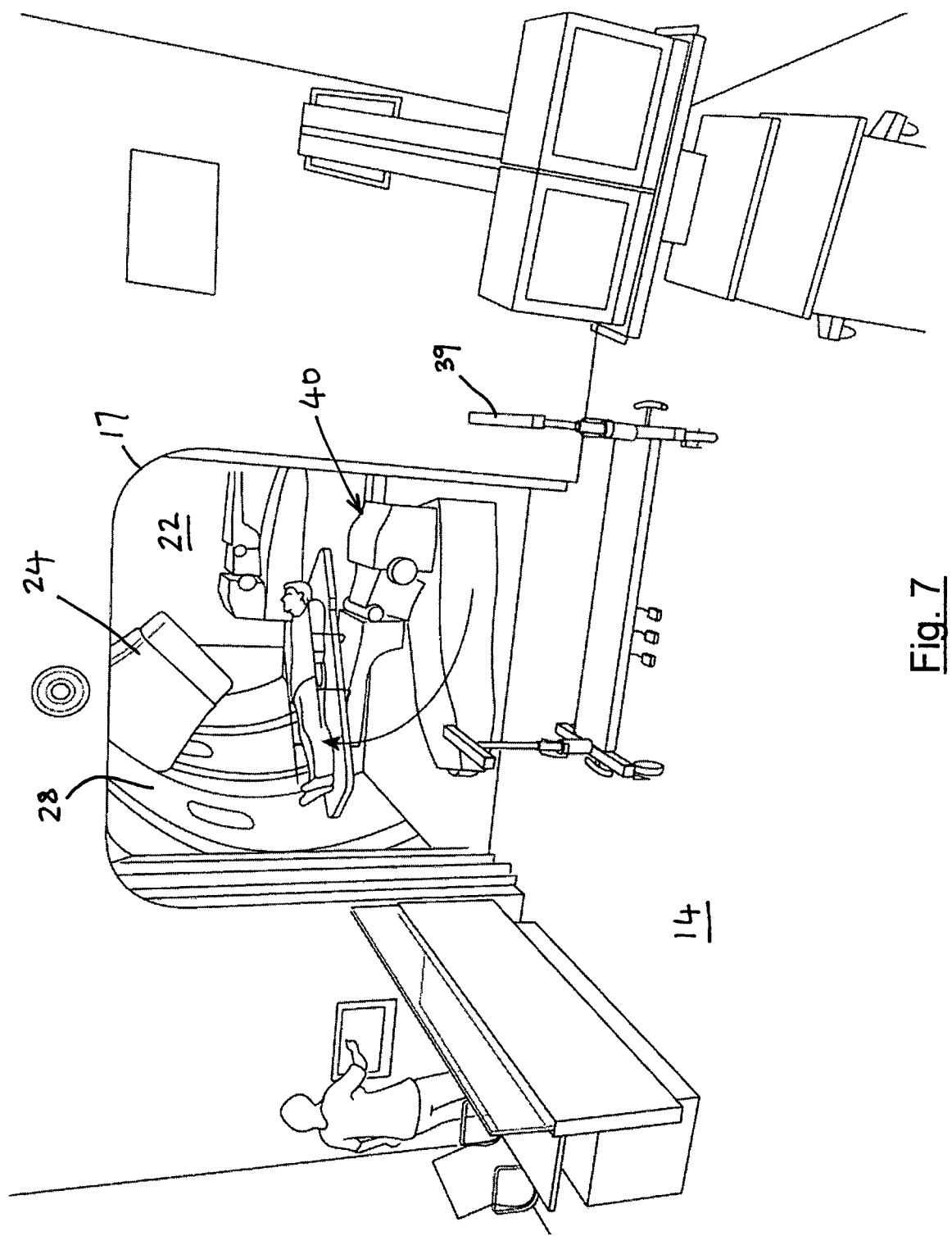
FIG. 7 is a second view of the waiting room and the treatment room of FIG. 6.

The particle accelerator 16 has an output device, typically comprising a nozzle 24, for delivering the radiation beam to the radiation target, i.e. a patient 26 (see FIGS. 6 and 7). The nozzle 24 may be configured to bend, scan, focus or otherwise manipulate the radiation beam at the point of delivery, and to this end may include one or more bending, scanning and/or focusing magnets (and/or other beam forming and/or beam manipulating and/or energy selection components as required) for energy selection, bending, scanning and/or focusing the radiation beam at the point of delivery as required. Optionally, the nozzle 24 may be extendible in its longitudinal direction. The nozzle 24 may comprise any conventional radiation therapy beam delivery nozzle. Typically, the nozzle 24 is fixed with respect to the particle accelerator 16 so that it moves with the particle accelerator 16. In preferred embodiments there is no beam transport system between the particle accelerator 16 and the nozzle 24, in particular no beam transport system that bends the radiation beam between the particle accelerator 16 and the nozzle 24. This may be achieved by aligning the nozzle 24 with the particle beam produced by the accelerator 16. This arrangement simplifies the beam delivery system 12, reducing cost and increasing reliability. It will be seen that in preferred embodiments, positioning the particle beam with respect to the patient 26 involves moving the whole accelerator 16, and therefore the nozzle 24.

The system 10 includes a treatment structure, or treatment pod 20, that is shaped and dimensioned to define an internal treatment room 22 for receiving the patient 26. The term pod is intended to embrace any structure, typically comprising an enclosure or chamber, that is shaped and dimensioned, and/or otherwise configured, to define an internal treatment room 22 for receiving the patient. The treatment pod 20 comprises a hollow body structure 28 that defines the treatment room 22. The preferred body structure 28 comprises a solid sleeve-like wall extending around a longitudinal (or end-to-end) axis of the pod 20 and enclosing the treatment room around the longitudinal axis. Alternatively, the body structure 28 may be open or partially open, e.g. being cage-like or comprising an open or partially open frame. The longitudinal, or end-to-end, axis of the pod 20 typically corresponds with the longitudinal, or end-to-end axis of the room 22. At least one longitudinal end 29A, 29B of the body structure 28 is open to provide access to the treatment room 22 for a patient, medial worker and/or equipment as required. The, or each, end 29A, 29B may be completely open, or open in that a doorway is defined, as desired. The, or each, end 29A, 29B may optionally include one or more closable doors for allowing or preventing access to the room 22 via the respective end 29A, 29B. Accordingly, one or both ends 29A, 29B of the pod 20 may service as an entrance to and exit from the room 22. In the illustrated embodiment, both ends 29A, 29B are open. Alternatively, one end 29A, 29B may be closed by a wall or other solid structure. The body structure 28, or at least part of it, may be substantially cylindrical in shape, but may alternatively take any other desired shape. The body structure 28 may be formed from any suitable material, for example metal, plastics or a composite material. Optionally, the body structure 28 is formed form, or is cladded with, radiation shielding material.

The beam delivery system 12 is carried by the treatment pod 20 and arranged to deliver the radiation beam to the treatment room 22, and in particular towards a treatment location in the room 22. In particular, the nozzle 24 (at least its delivery end) is located within the treatment room 22, and is arranged to direct the particle beam into the treatment room 22, in particular towards the treatment location in the room 22. In use, a patient support apparatus is located at the treatment location and a patient supported thereby is targeted by the nozzle 24 in order to receive particle beam therapy. The nozzle 24 is preferably arranged to deliver the radiation beam radially into the room 22, i.e. towards a centrally located point or axis, e.g. the central longitudinal, or end-to-end, axis of the room 22 or pod 20. Advantageously, the particle accelerator 16 is located externally of the treatment pod 20. In preferred embodiments, the beam delivery system 12 is mounted on, or otherwise coupled to, the body structure 28, preferably with the particle accelerator 16 located outside of the body structure 28 and the nozzle 24 extending through the body structure 28 such that its delivery end is located in the treatment room 22. Alternatively, the pod 20 may include a support structure (not illustrated), which may be separate from the body structure 28, for supporting the beam delivery system 12, and in particular for supporting the particle accelerator 16 externally of the body structure 28. In any event, the beam delivery system 12, including the particle accelerator 16 is carried by the pod 20.

Advantageously, the beam delivery system 12, including the particle accelerator 16, is movable with respect to the pod 20, and in particular with respect to the treatment room 22. This enables the position, preferably the orientation, of the radiation beam to be adjusted with respect to the treatment room 22, and in particular the treatment location. The preferred arrangement is such that the beam delivery system 12 is moveable, at least partly and optionally fully, around the pod 20 and around the treatment room 22, preferably in an orbital manner, and in particular around the treatment location in the treatment room. In preferred embodiments, the particle accelerator 16 is correspondingly movable around the outside of the treatment room 22. The nozzle 24 is movable correspondingly around the inside of the treatment room 22. The preferred arrangement is such that the nozzle 24 (and in particular its delivery end) is movable around the treatment location within the treatment room 22, preferably along an arc-like or circular path. The beam delivery system 12 may be coupled to the pod 20, preferably to the body structure 28, by any conventional coupling mechanism(s) that allow the desired movement of the beam delivery system 12 with respect to the pod. In the illustrated embodiment, the beam delivery system 12 is moveable in a single plane around the pod 20, but in alternative embodiments may be rotatable around the pod 20 in more than one plane.

In preferred embodiments, the beam delivery system 12 is rotatable about an axis of the pod 20. The axis is spaced apart from the beam delivery system 12, and in particular the particle accelerator 16, such that the rotation is of an orbital nature. Preferably, the rotation axis is the longitudinal axis or other end-to-end axis, of the pod 20 or treatment room 22, preferably the central longitudinal or end-to-end axis. Preferably, the beam delivery system 12 is rotatable through 360° around the axis. However, the beam delivery system 12 may be rotatable by any amount up to 360° around the axis depending on the requirements of the application. Correspondingly, the nozzle 24 may target the patient from any direction through up to 360° around the axis. In preferred embodiments the arrangement is such that, as the beam delivery system 12 rotates, the particle accelerator 16 revolves around the outside of the pod 20 while the nozzle 24 correspondingly revolves around the inside of the pod 20 in the treatment room 22.

In preferred embodiments, the beam delivery system 12 is coupled to an annular section 28C of the body structure 28 that is rotatable about the longitudinal axis of the pod 12. The beam delivery system 12 may be mounted on the rotatable section 28C so that it rotates with the rotatable section 28C. The rotatable section 28C may be located between, and rotatable with respect to, first and second non-rotatable end sections 28A, 28B of the body structure 28. The rotatable section 28C may be coupled to each end section 28A, 28B by any conventional rotatable coupling mechanism 27, which may for example comprise a slewing bearing. In preferred embodiments, the particle accelerator 16 is mounted on the outside of the rotatable body section 28C, and the nozzle 24 extends through the rotatable body section 28C such that its beam delivery end is located inside the body section 28C.

The beam delivery system 12 may be mounted on the rotatable body section 28C by any conventional mounting means. In the illustrated embodiment, the particle accelerator 16 is mounted on the external surface of the body section 28C by one or more supports 25A, 25B. The particle accelerator 16 may be fixed with respect to the body section 28C. Alternatively, the particle accelerator 16 may be rotatable with respect to the body section 28C about a central axis of the accelerator 16 that runs parallel with the longitudinal axis of the pod 20. For example, the accelerator 16 may be fixedly or rotatably mounted between supports 25A, 26B as desired.

In alternative embodiments (not illustrated), the whole body structure 28 may be rotatable as described above in respect of the body section 28C, in which case the beam delivery system 12 may be coupled to the body structure 28 for rotation with the body structure 28 as described above with respect to the body section 28C. In such embodiments, the pod 20 may include a support structure for the body structure 28, the body structure 28 being rotatably coupled to the support structure by any conventional rotating coupling mechanism(s) to allow rotation about the longitudinal axis of the pod 20. Alternatively still, the body structure 28 may be static and the beam delivery system 12 may move around the body structure 28, and therefore around the treatment room 22. In such embodiments, the pod 20 may include a support structure for the beam delivery system 12, the beam delivery system 12 being movably coupled to the support structure by any conventional coupling mechanism(s) to allow movement of the beam delivery system 12 around the body structure 28 and therefore around the treatment room 22.

In preferred embodiments, the pod 20 includes a floor structure 30 within the body structure 28, providing a floor for the treatment room 22. The floor structure 30 is fixed with respect to the pod 20 such that as the beam delivery system 12 moves, it moves with respect to the floor structure 30, and therefore with respect to the treatment room 22. The floor structure 30 may be supported by the end sections 28A, 28B of the body structure 28, or by any other convenient support structure. Depending on the embodiment, all or part 28C of the body section may rotate with respect to the floor structure 30.

In preferred embodiments, the movement of the beam delivery system 12 around the pod 20 is counterbalanced. The preferred treatment pod 20 includes a counterbalance 32 arranged to counterbalance the beam delivery system 12 with respect to the longitudinal axis of the pod 20, or other axis about which it is rotatable or pivotable. In preferred embodiments, the counterbalance 32 counterbalances the rotational movement of the beam delivery system 12 around the pod 32, in particular about the longitudinal axis of the pod 20. The mass and location of the counterbalance 32 is such that it provides a counterbalancing moment to that imparted the beam delivery system 12 with respect to the rotational axis, which is conveniently the longitudinal axis of the pod 12. This facilitates rotation of the beam delivery system 12 in that less driving force is required to rotate the beam delivery system 12 than would be required if there was no counterbalance. It is noted that an exact counterbalancing moment is preferred, but the counterbalance 32 does not need to exactly counterbalance the beam delivery system 12.

In preferred embodiments, the counterbalance 32 is rotatable about the longitudinal axis of the pod together with the beam delivery system 12, and is preferably located opposite to the beam delivery system 12 with respect to the longitudinal axis of the pod 20. As such the beam delivery system 12 and counterbalance 32 may be radially spaced-apart around the longitudinal axis of the pod 20 by 180°, or approximately 180°. In preferred embodiments, the counterbalance 32 is mounted on, or otherwise coupled to, the body structure 28, and is preferably located outside of the body structure 28. In preferred embodiments, the counterbalance 32 is mounted on the rotatable section 28C so that it rotates with the rotatable section 28C. In the illustrated embodiment, the counterbalance 32 is mounted on the external surface of the body section 28C by one or more supports 31A, 31B. In typical embodiments, substantially all of the weight of the beam delivery system 12 is provided by the particle accelerator 16 and so it may be said that the counterbalance 32 counterbalances the particle accelerator 16. Typically, the counterbalance 32 is located externally of the pod 20, opposite the particle accelerator 16 with respect to the longitudinal axis of the pod 20.

The counterbalance 32 may comprise any convenient object or objects with a suitable mass. Optionally, the counterbalance 32 may comprise a second beam delivery system (not illustrated), which may be the same as or similar to the beam delivery system 12, and may be coupled to the treatment pod 20 in the same or a similar manner. In particular, the counterbalance 32 may comprise the particle accelerator of a second beam delivery system. The particle accelerator of the second beam delivery system may be of the same type as the particle accelerator 16 of the first beam delivery system 12, or may be of a different type, i.e. capable of providing the same type or a different type of therapy. Providing a second beam delivery system allows a patient in the treatment room 22 to be treated by either or both beam delivery systems, simultaneously or in turn as desired, as well as allowing the patient to be subjected to two different types of therapy in the same session. The first and second beam delivery systems are radially spaced apart around the longitudinal axis of the pod 20, preferably by 180°, or approximately 180°. This spacing allows the patient to be treated from corresponding different directions by the respective nozzles 24. Also, the spacing allows one or other of the nozzles 24 to target the patient from any direction through 360° around the longitudinal axis without either of the beam delivery systems having to be rotated through more than 180°. Optionally, therefore, the rotation of the beam delivery systems about the longitudinal axis may be restricted to 180°, or approximately 180°.

More generally, in alternative embodiments (not illustrated), two or more beam delivery systems may be coupled to the treatment pod 20, radially spaced apart around the longitudinal axis of the pod 20. The beam delivery systems are preferably provided with a respective counterbalance, optionally as one or more counterbalancing pair of beam delivery systems, as described above. Each beam delivery system may be the same as or similar to the beam delivery system 12, and may be coupled to the treatment pod 20 in the same or a similar manner as described above.

In preferred embodiments, the treatment pod 20 includes at least one drive mechanism for moving the beam delivery system 12 around the pod 20, which typically involves rotating the beam delivery system 12 about the longitudinal axis of the pod 20. The drive mechanism(s) may take any suitable conventional form. In the illustrated embodiment, a drive mechanism 34 is coupled between the rotatable body section 28C and one of the end sections 28B, and is arranged to rotate the body section 28C with respect to the end section 28B. In this example, the drive mechanism 34 comprises a motor 34A mounted on the rotatable body section 28C, and a rotatable driving head 34B coupled to the end section 28A, whereby rotation of the driving head 34B causes rotation of the rotatable body section 28C with respect to the end section 28B.

In preferred embodiments, the radiation therapy system 10 includes a bay structure 60, or other housing structure, typically a building structure, for housing the treatment pod 20. Preferably, the treatment pod 20 is supported, by any convenient conventional support means, above the floor 61 of the bay 60 to provide sufficient space below the treatment pod 20 to accommodate the particle accelerator 16 and/or the counterbalance 32 as the beam delivery system 12 rotates.

The preferred radiation therapy system 10 includes a plurality of waiting rooms 14. The preferred arrangement of the system 10 is such that a patient 26 (FIGS. 6 and 7) can be transferred directly from any one of the waiting rooms 14 into the treatment room 22. Each waiting room 14 has a doorway 17, and optionally a door 19 for opening and closing the doorway 17. In embodiments where the waiting room 14 has a door 19, the or each open end 29A, 29B of the pod 20 does not require a door, although may have a door (not illustrated) if desired. In embodiments where the or each end 29A, 29B of the pod 20 has a door, the doorway 17 of each waiting room 14 does not require a door, although may have a door 19 if desired. The door 19 and/or the door provided on the pod 20 (when present) may comprise radiation shielding.

In preferred embodiments, the treatment pod 20 is open to provide user access from each end 29A, 29B, and the waiting rooms 14 are arranged in one or more oppositely disposed pairs 14A, 14B. The waiting rooms 14A, 14B of the, or each, pair are spaced apart with their respective doorway 17 facing each other, and preferably in register with one another. The spacing between the opposing waiting rooms 14A, 14B is sufficient to allow the treatment pod 20 to be located between the opposing rooms 14A, 14B, with one end 29A facing one of the waiting rooms 14A and the other end 14B facing the other waiting room 14B. When the treatment pod 20 is located between the opposing waiting rooms 14A, 14B, the open end 29A is aligned with the doorway 17 of waiting room 14A, and the open end 29B is aligned with the doorway 17 of waiting room 14B. The preferred arrangement (e.g. the relative length of the pod 20 and the gap between the waiting rooms 14A, 14B) is such that the respective pod opening and waiting room doorway 17 are adjacent one another such that there is direct access between the respective waiting room 14A, 14B and the treatment room 22 via the respective pod end 29A, 29B.

In one embodiment, the system 10 has a single pair of waiting rooms 14A, 14B and the treatment pod 20 is statically installed between them in the manner described above.

In preferred embodiments, the treatment pod 20 is movable with respect to the treatment rooms 14, so that it may be aligned with one or two treatment rooms 14 at a time, depending on the configuration of the system 10. In preferred embodiments, and as illustrated in the embodiment of FIGS. 1 to 5, the treatment pod 20 is movable so that it may be aligned with any one pair of a plurality of pairs of opposing treatment rooms 14A, 14B. When aligned with a pair of treatment rooms 14A, 14B, the pod 20 is located between them as described above to allow access to the treatment room 22 from either of the waiting rooms 14A, 14B with which it is aligned.

In the illustrated embodiment, three pairs of opposing waiting rooms 14A, 14B are shown, although in alternative embodiments there may be more or fewer pairs of opposing waiting rooms 14A, 14B. The pairs of opposing waiting rooms 14A, 14B are preferably arranged in a linear array to define a common linear passage 63 running between all of pairs of opposing waiting rooms 14A, 14B. The pod 20 is located in the linear passage 63 and is movable along the linear passage 63 so that it may align with any one of the opposing pairs of waiting rooms 14A, 14B. In preferred embodiments, the bay 60 is shaped and dimensioned to provide the linear passage 63, with opposing waiting rooms 14A, 14B being located along opposite sides of the passage 63. In an alternative embodiment (not illustrated), a plurality of waiting rooms 14 may be provided along one side of the passage 63 only, the pod 20 being movable along the passage 63 to align with only one waiting room 14 at a time, in which case the pod 20 may be closed at its other end. Alternatively still, one or more waiting rooms 14 may be provided on each side of the passage 63, but not necessarily arranged in opposing pairs, in which case the pod 20 is only able to align with one waiting room 14 at a time.

The passage 63 need not necessarily be linear. In alternative embodiments, the bay 60 may be shaped to define a circular, semi-circular passage or otherwise curved or curvilinear passage (not illustrated). In any case, one or more waiting rooms 14 may be provided along either one or both sides of the passage 63, and the pod 20 is movable along the passage 63 to align with one or two waiting rooms at a time. In cases where waiting rooms 14 are provided on both sides of the passage 63, it is preferred that they are arranged in opposing pairs so that the pod 20 can align with two waiting rooms simultaneously.

The treatment pod 20 may be movable along the passage 63 by any conventional conveyancing means. In typical embodiments, conveyancing means comprises a carriage 64 on which the treatment pod 20 is mounted. The carriage 64 may be of any conventional type, for example comprising wheels, rollers, runners or tracks, as is convenient. The bay 60 may include one or more tracks 66 along which the carriage 64 may run. In the illustrated embodiment, a respective track 66A, 66B runs along each side of the passage 63. The carriage 64 may comprises first and second parts 64A, 64B, one for each of the tracks 66A, 66B. The tracks 66A, 66B are preferably located above the floor level of the bay 60 such that the carriage 64 supports the pod 20 above the floor level of the bay 60. Hence, the conveyancing means can conveniently provide the support means for supporting the treatment pod 20 above the floor 61 of the bay 60 to provide sufficient space below the treatment pod 20 to accommodate the particle accelerator 16 and/or the counterbalance 32 as the beam delivery system 12 rotates. One or more drive mechanisms 68 may be provided for moving the carriage 64 along the passage 63. The drive mechanisms 68 may be of any suitable conventional type.

In alternative embodiments (not illustrated), any other suitable conveyancing means may be used to move the treatment pod 20 with respect to the waiting rooms 14. For example, the conveyancing means may comprise a movable gantry, or a gantry crane, or a jib, or an arrangement of linear actuators, e.g. hydraulic actuators.

In alternative embodiments (not illustrated), the bay 60 need not necessarily define a passage for the pod 20 to move along. For example, the bay 60 may comprise a room around which the pod 20 is movable by any suitable conveyancing means. A plurality of waiting rooms 14 may be arranged around the outside of the bay room, the pod 20 being movable around the bay room so that it aligns with any one of the waiting rooms 14 at a time. The room may be circular, or at least have an arc-shaped wall, so that the waiting rooms 14 are arranged in a circle or arc around the bay room. The pod 20 may be carried by a rotatable support that is configured to move the pod 20 from waiting room to waiting room. For example, one end of the pod 20 may be coupled to the support in a cantilevered or jib manner, so that rotation of the support moves the other end of the pod in an arc, or circle, from room to room.

In the illustrated embodiment, the waiting rooms 14 are provided in a single level or storey. In alternative embodiments (not illustrated), the waiting rooms 14 may be provided in a multi-storey structure. Accordingly, the treatment pod 20 may be carried by a lift device for raising and lowering the pod 20 between storeys. Any conventional lift device may be used for this purpose. The arrangement of the bay and waiting rooms of each storey may be the same or similar to any of the arrangements described above.

The waiting rooms 14 and bay 60 are typically provided in a building structure, such as a hospital or clinic.

Referring now in particular to FIGS. 6 and 7, the inside of a typical waiting room 14 is shown. It will be understood that specific equipment and furnishings are shown by way of example only. The waiting room 14 aligned with the treatment pod 20 and the door 19 is open to allow access between the waiting room 14 and the treatment room 22.

At least one patient support apparatus 38 is provided, preferably at least one for each waiting room 14. The patient support apparatus 38 may take any conventional form, typically comprising a chair, couch, platform or bed, for accommodating the patient 26. The preferred support apparatus 38 provides at least one of, and may be operable between any two or more of, the following configurations: a standing configuration (in which it supports the patent in a standing position), a sitting configuration (in which it supports the patient in a sitting position), a fully reclined configuration (in which it supports the patient in a fully reclined position), and one or more semi-reclined configurations. In the illustrated embodiment, the patient support apparatus 38 comprises a platform on which the patient 26 can lie flat. In FIG. 6, the platform 38 is shown supported on a trolley 39.

The preferred system 10 includes at least one actuation apparatus 40 for moving the patient support apparatus 38 between the waiting room 14 and the treatment room 22 (as illustrated in FIG. 7). The actuation apparatus 40 is preferably operable to move the patient support apparatus 38 to a treatment location in the treatment room 22 where the nozzle 24 of the, or each, beam delivery system 12 can direct its beam onto the patient 26.

In the illustrated embodiment, the actuation apparatus 40 is provided in the treatment room 22 and is operable to extend out of the treatment room 22 into the waiting room 14 to fetch the patient support apparatus 38. Alternatively, the patient support apparatus 38 may be integrally formed with the actuation apparatus 40 and the actuation apparatus may be operable to extend out of the treatment room 22 into the waiting room 14 to fetch the patient 26. These arrangements allow the door(s) between the treatment room 22 and waiting room 14 to be closed during therapy. In preferred embodiments where the pod 20 may be accessed from both ends 29A, 29B, a respective actuation apparatus 40 (with or without an integral patient support apparatus) may be provided for each end 29A, 29B, as illustrated in FIGS. 6 and 7. Alternatively, the actuation apparatus 40 may be provided in the waiting room 14 and be operable to extend into the treatment room 22. In alternative embodiments, the actuation apparatus may be omitted and the patient support apparatus 38 may be installed in the treatment room 22, preferably at the treatment location.

The actuation apparatus 40 may be configured in any conventional manner in order to achieve the desired movability of the patient support apparatus 38. By way of example, in the illustrated embodiment the actuation apparatus 40 comprises an articulated arm 44. Typically, the actuation apparatus 40 is power operated, e.g. by one or more power operated actuators (not shown), which may for example be electrically or hydraulically operated as is convenient, and may be linear or rotary as required.

When in the treatment location, it is preferred that the patient support apparatus 38 is adjustable to adjust the position of the patient 38 with respect to the nozzle(s) 24. In preferred embodiments, the patient support apparatus is operable to move the patient 26 linearly along any one or more of the three orthogonal Cartesian axes, and/or rotate the patient 26 about any one or more of the three orthogonal Cartesian axes. The supported movements may be effected by the patient support apparatus 38 self, and/or by the actuation apparatus 40 as is convenient. In addition, the nozzle(s) 24 is movable with respect to the treatment location, and therefore the patient 26, by rotating the beam delivery system 12 as described above, and/or by adjustment of the nozzle 24. This facilitates a wide range of relative angles and positions of the delivered radiation beam relative to the patient support apparatus when in the treatment location. In preferred embodiments, the adjustability of the patient support apparatus 38 and/or of the beam delivery system 12 individually or together allow the radiation beam to be delivered in a precise and highly adjustable manner (advantageously in up to 6 cartesian dimensions $(x,y,z,\theta,\phi,\psi)$) to a target zone in the treatment location. In particular it is preferred the radiation beam may be targeted at the target zone 3 dimensionally. Advantageously, the adjustability of the beam delivery system 12 is configured to provide isocentric delivery of the radiation beam to the target zone (which target zone coincides in use with a patient on the relevant patient support apparatus 38). Advantageously, during use the relative positions and angles of the system 10 may be adjusted to achieve isocentric irradiation of the target zone. Advantageously, the system 10 allows substantially full 3-D Isocentric irradiation of a patient, suitable for intensity modulated therapy or spot scanning. Scanning of the radiation beam about at least one and preferably two perpendicular axes (e.g. a vertical axis and a perpendicular horizontal axis running transversely of the room) may be supported, conveniently by incorporation of scanning magnets in the nozzle 24.

Systems 10 embodying the invention typically include a control system (not shown), which may be located in a separate room. The control system may include equipment for controlling and monitoring any aspect of the system 10 and may take any suitable conventional form, typically including suitable programmed computing device(s). The control system typically includes means for controlling and/or monitoring the operation of any one or more of the beam delivery system 12 (including its rotation and its beam delivery), pod conveyancing means, the actuation apparatus 40, the patient support apparatus 38 and the doors 19 as applicable. The control system may include components (e.g. scanner(s), visual display unit(s) and user interface device(s)) of an imaging system for controlling and/or monitoring operation of the system 10. The imaging system may comprise any one or more of an MRI system, PET system, SPECT system or CT system. The control system may be configured to control any one or more components of the system 10 collectively or individually.

During use, the control system may obtain treatment information in respect of the waiting room 14 to be serviced. The treatment information typically includes beam delivery vector(s) for targeting the beam on a target zone, and dosage information. The control system causes the pod 20 to align with the respective waiting room, and positions the particle accelerator 16, including the nozzle 24, in a desired position and/or orientation as determined from the treatment information, i.e. in order to deliver the radiation beam at the required delivery vector(s). 3D targeting of the radiation beam may be performed by a laser so that the radiation beam always impinges on the target zone as desired.

In preferred embodiments, the control system includes one or more devices (e.g. cameras and/or motion sensors and/or pressure sensors) for detecting movement of the patient when on the patient support apparatus 38. The control system may be configured to use any detected movement of the patient to re-position one or more component of the system 10, in particular of the beam delivery system 12, to ensure that the radiation beam is correctly targeted on the patient, i.e. the delivery of the beam automatically tracks any detected movement of the patient during use. Optionally, if any detected movement exceeds a threshold level, then the control system may be configured to cease treatment.

The provision of a counterbalanced beam delivery system 12 is advantageous in that it allows the particle accelerator 16 to be easily moved in the manner described, which would be beyond the capability of conventional robots since particle accelerators can weigh between 100-200 tonnes and so are conventionally deployed statically.

Providing the nozzle 24 at the particle accelerator 16 without an intermediate beam transport system is advantageous since it avoids or reduces beam degradation and collateral residual radiation that can be caused by bending magnets and other components of a beam transport system. Moreover, as there is no long beam line or 2D gantry, the maintenance, energy requirements, size, scale and costs of the system are reduced in comparison with conventional systems.

Providing one or more beam delivery system 12 on a pod 20 that can service multiple waiting rooms 14 allows efficient use of the treatment room 22, particularly since multiple patients can be prepared for therapy simultaneously and wait for the treatment room 22 to become available.

Figure 8:
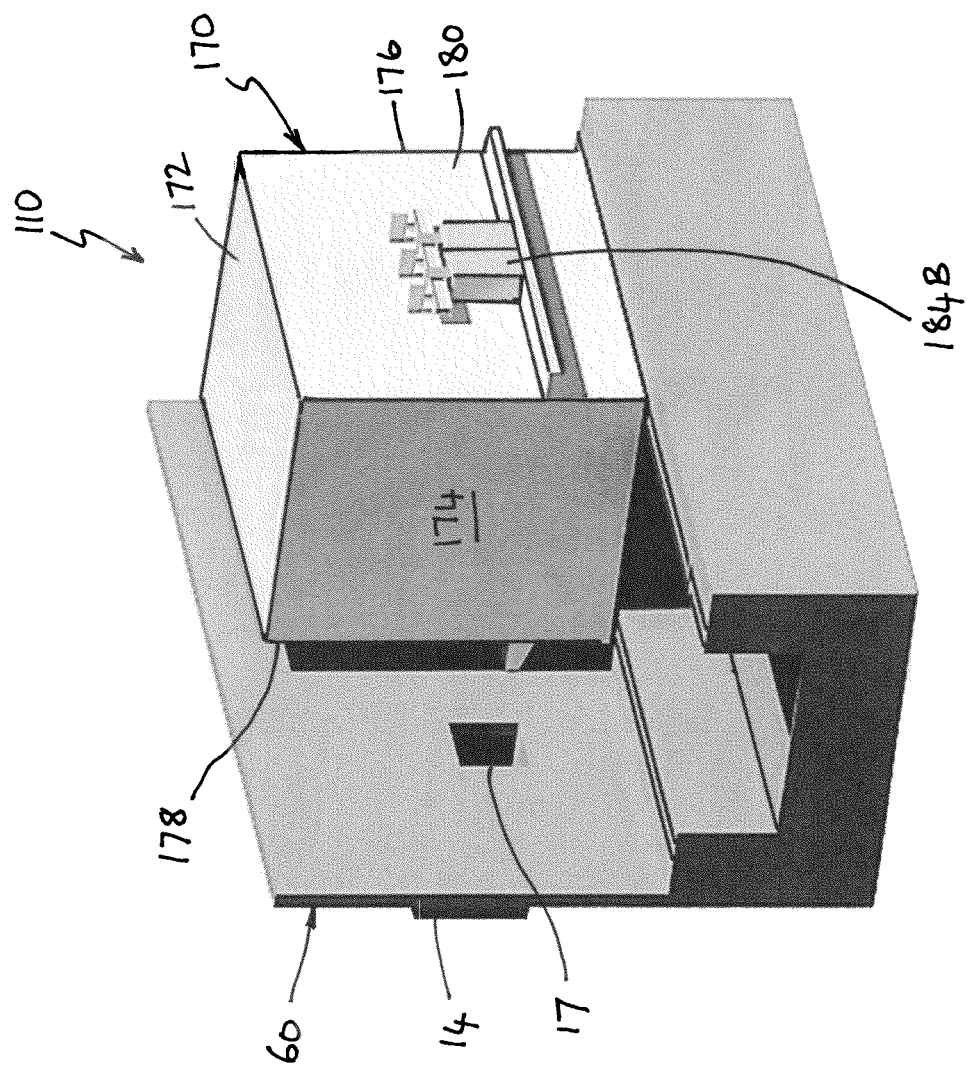
FIG. 8 is a perspective view of an alternative embodiment of a radiation therapy system according to the invention.
Figure 9:
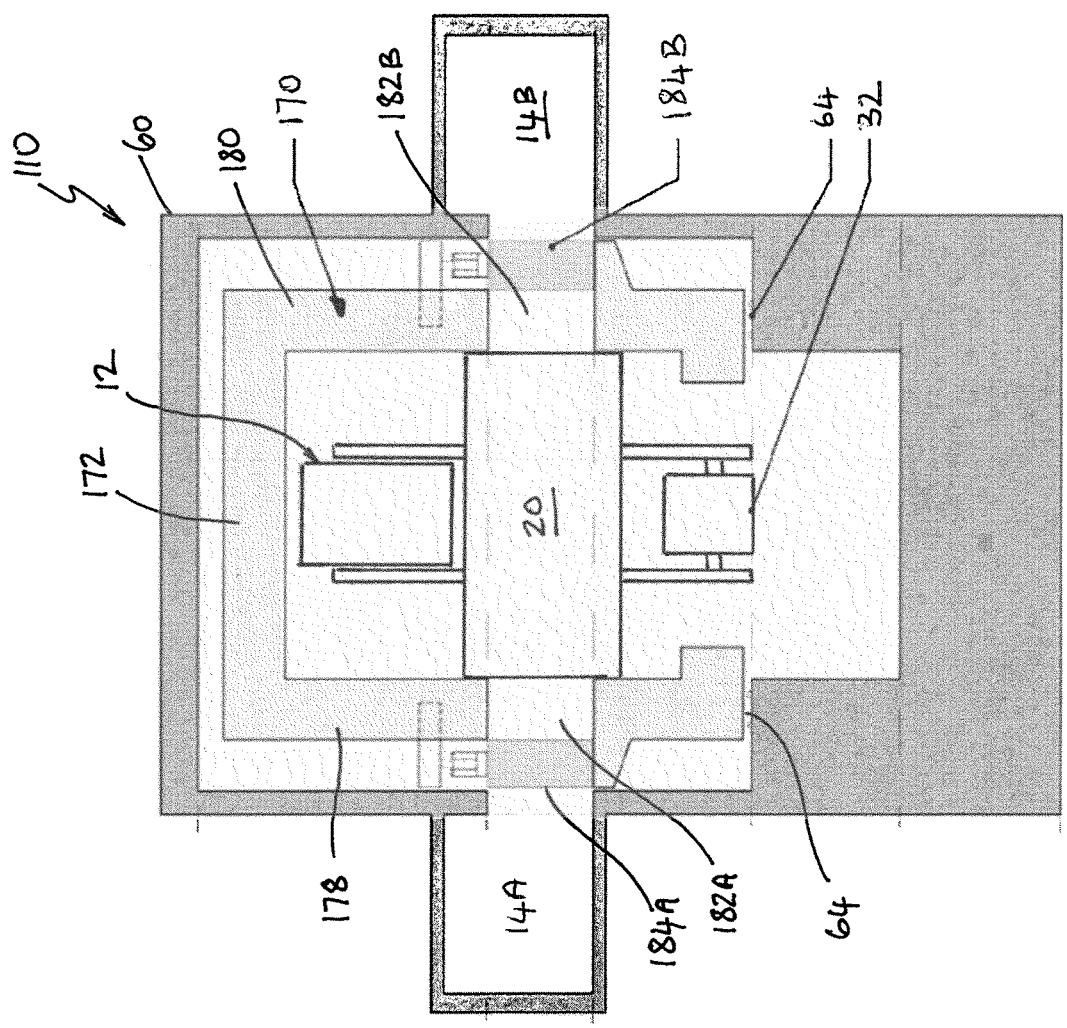
FIG. 9 is a sectioned end view of the system of FIG. 8.
Figure 10:
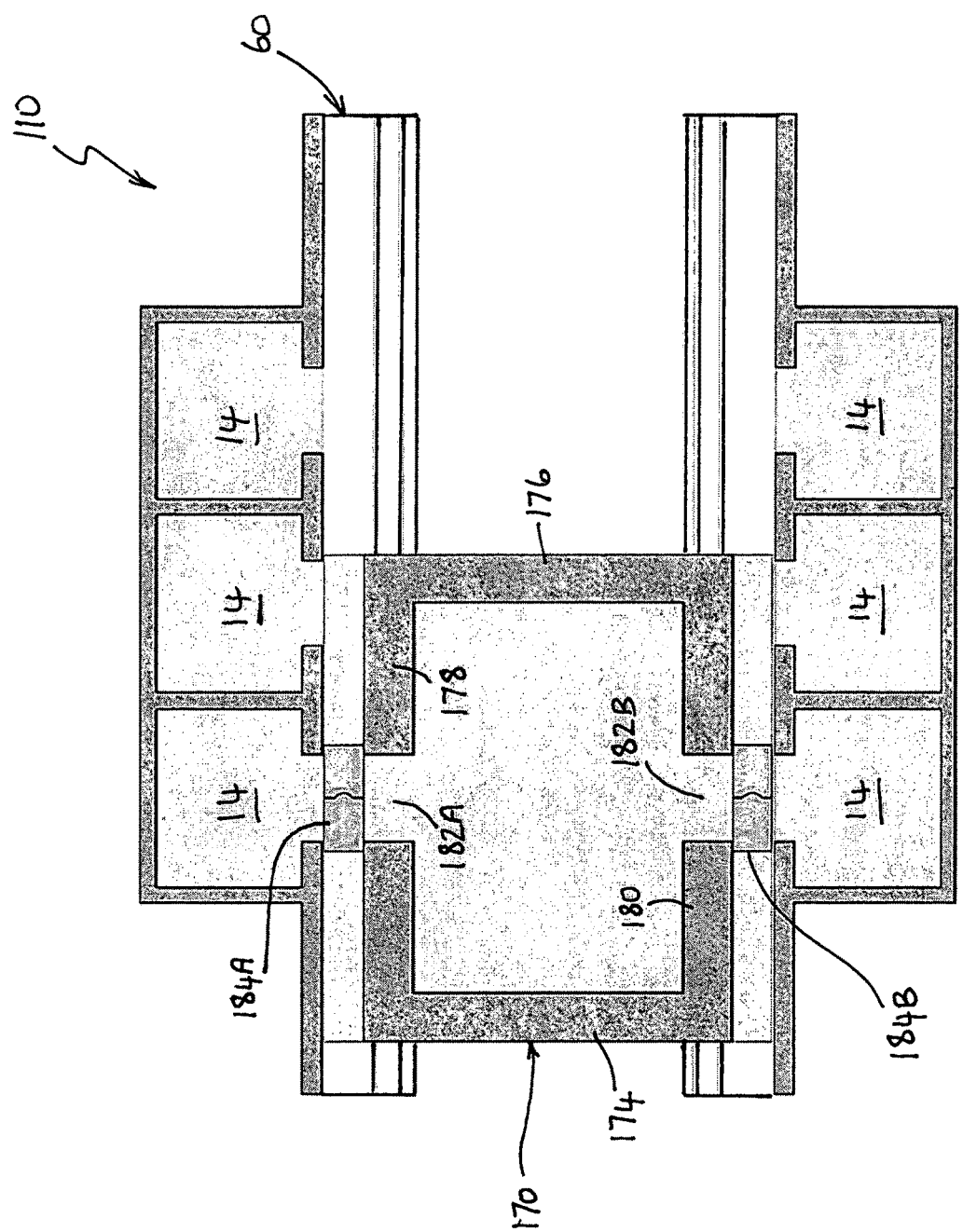
FIG. 10 is a sectioned plan view of the system of FIG. 8.

FIGS. 8 to 10 illustrate another radiation therapy system 110 embodying the invention. The radiation therapy system 110 is similar to the radiation therapy system 10, like numerals being used to denote like parts and the same or similar description applying as would be apparent to a skilled person. FIGS. 8 to 10 illustrated a preferred radiation shielding configuration for the radiation therapy systems embodying the invention. The system 110 includes a radiation shielding structure 170 that surrounds, or at least partly surrounds, the treatment pod 20 and the beam delivery system 12, and is shaped and dimensioned accordingly. The preferred radiation shielding structure 170 has a top shield section 172 located so as to provide radiation shielding above the treatment pod 20 and beam delivery system 12; first and second side shield sections 174, 176 located so as to provide radiation shielding at opposite sides, respectively, of the treatment pod 20 and the beam delivery system 12, and first and second end shield sections 178, 180, located so as to provide radiation shielding at opposite ends, respectively, of the treatment pod 20 and the beam delivery system 12. The radiation shielding structure 170 may be box-like in shape, e.g. may be substantially rectangular in transverse and longitudinal cross-section. The preferred configuration is such that the radiation shielding structure 170 encloses the treatment pod 20 and the beam delivery system 12 at least from above, at opposite sides and at opposite ends. In the illustrated embodiment, the shield structure 170 is open at its bottom, i.e. below the treatment pod 20 and the beam delivery system 12. Alternatively, the radiation shield structure 170 may include a bottom section located to provide radiation shielding below the treatment pod 20 and the beam delivery system 12.

In preferred embodiments in which the assembly of the treatment pod 20 and the beam delivery system 12 are movable, the radiation shielding structure 170 moves with the assembly. The conveyancing means 64 may be embedded within the structure 170, or encased by it, or located outside of it as is convenient.

In preferred embodiments, the radiation shielding structure 170 comprises a doorway 182A, 182B aligned with each doorway of the treatment pod (i.e. the doorways at ends 29A, 29B in the illustrated embodiment) with a respective door 184A, 184B. The doors 184A, 184B are formed at least partly from radiation shielding material such that they serve as part of the radiation shielding structure 170. For example, the doorways 182A, 182B and doors 184A, 184B may be incorporated in to a respective end section 178, 180 of the shielding structure 170. Conveniently, the doors 184A, 184B serve as doors to the pod structure 20 and so additional doors at the ends 29A, 29B are not required.

The radiation shielding structure 170 may be formed from any suitable conventional radiation shielding material, e.g. polyethylene, borated polyethylene, concrete and water.

The radiation shielding structure 170 is advantageous in that it obviates the need to provide radiation shielding throughout the bay structure 60 or other structure that surrounds the assembly, and means that the each waiting room 14 does not need to have its own radiation shielding door.

Although embodiments of the invention are described herein in the context of a radiation therapy system having a beam delivery system comprising a particle accelerator for generating a radiation beam, the invention may alternatively be used with other beam delivery systems that do not include a particle accelerator, instead comprising means for generating other types of beam, e.g. an ultrasound beam. Alternatively, the beam delivery system may be replaced by an alternative patient treatment system or patient scanning system, e.g. MRI scanning equipment or CT scanning equipment.

The invention is not limited to the embodiment(s) described herein but can be amended or modified without departing from the scope of the present invention.

The invention claimed is:

1. A radiation therapy system comprising:
a treatment pod comprising a hollow body structure that defines an internal treatment room, the pod having first and second ends either one or both of which includes a doorway that provides access to the treatment room;
a beam delivery system comprising a particle accelerator for generating a radiation beam; and
a radiation shielding structure at least partly surrounding the treatment pod and the beam delivery system, the radiation shielding structure comprising at least one doorway aligned with a respective doorway of the treatment pod, said at least one doorway of the radiation shielding structure having at least one door formed at least partly from radiation shielding material;
wherein said beam delivery system is carried by said treatment pod and is configured to deliver said radiation beam to said treatment room;
wherein said beam delivery system is movable with respect to the treatment pod in order to adjust the position of said radiation beam with respect to said treatment room; and
wherein the system further includes a plurality of waiting rooms, said treatment pod being aligned with, or movable together with the beam delivery system and at least said at least one door of the radiation shielding structure into alignment with, each of said waiting rooms to allow access to the treatment room from each waiting room via said first or second end.

2. The system of claim 1, wherein the beam delivery system is moveable at least partly around the pod and around the treatment room in an orbital manner.

3. The system of claim 1, wherein said beam delivery system is rotatable about an end-to-end axis of said treatment pod.

4. The system of claim 1, wherein said particle accelerator is located externally of the treatment pod.

5. The system of claim 1, wherein said beam delivery system includes a beam delivery nozzle, and wherein said beam delivery nozzle is located inside said treatment room.

6. The system of claim 1, wherein the beam delivery system is carried by the hollow body structure with the particle accelerator located outside of the body structure and the beam delivery nozzle extending through the body structure.

7. The system of claim 6, wherein the body structure includes a rotatable section, the beam delivery system being coupled to said rotatable section, and wherein the body structure includes first and second end sections, said rotatable section being located between and rotatable with respect to said first and second end sections.

8. The system of claim 1, wherein the treatment pod includes a counterbalance arranged to counterbalance movement of the beam delivery system with respect to the treatment pod about a rotation axis, the counterbalance being rotatable around the pod together with the beam delivery system.

9. The system of claim 8, wherein the counterbalance is coupled to a rotatable section of said hollow body structure.

10. The system of claim 8, wherein said counterbalance comprises a second beam delivery system comprising a second particle accelerator for generating a second radiation beam, and being configured to deliver said second radiation beam into said treatment room.

11. The system of claim 1, wherein said waiting rooms are arranged in at least one pair of oppositely disposed waiting rooms, the respective waiting rooms of the, or each, pair being spaced apart with their respective doorway facing each other, and wherein said treatment pod is locatable between the respective waiting rooms of the, or each, pair to allow access to the treatment room from either of the respective waiting rooms.

12. The system of claim 11, wherein there is a single pair of oppositely disposed waiting rooms, the treatment pod being located between, and aligned with, each waiting room.

13. The system of claim 11, wherein there are multiple pairs of oppositely disposed waiting rooms, and wherein said treatment pod, together with the beam delivery system, is movable into alignment with any one of said pairs of waiting rooms.

14. The system of claim 11, wherein said plurality of waiting rooms are arranged in a linear, circular or curvilinear array, said treatment pod, together with the beam delivery system, being movable into alignment with any one of said waiting rooms to allow access to the treatment room from each waiting room.

15. The system of claim 11, further including conveyancing means for moving said treatment pod, together with the beam delivery system, into alignment with any one of said waiting rooms, or any two oppositely disposed waiting rooms.

16. The system of claim 11, wherein said waiting rooms are arranged in multiple stories, said system including a lift device for moving said treatment pod together with the beam delivery system between said stories.

17. The system of claim 1, further including a bay for housing the treatment pod, the treatment pod being supported above a floor of the bay to provide space below the treatment pod to accommodate the particle accelerator as the beam delivery system rotates.

18. The system of claim 1, wherein the radiation shielding structure comprises a top shield section located so as to provide radiation shielding above the treatment pod and beam delivery system; first and second side shield sections located so as to provide radiation shielding at opposite sides, respectively, of the treatment pod and the beam delivery system, and first and second end shield sections located so as to provide radiation shielding at opposite ends, respectively, of the treatment pod and the beam delivery system.

19. The system of claim 1, wherein the radiation shielding structure encloses the treatment pod and the beam delivery system at least from above, at opposite sides and at opposite ends.

20. A radiation therapy system comprising:
a treatment pod comprising a hollow body structure that defines an internal treatment room, the pod having first and second ends either one or both of which provides access to the treatment room; and
a beam delivery system comprising a particle accelerator for generating a radiation beam;
wherein said beam delivery system is carried by said treatment pod and is configured to deliver said radiation beam to said treatment room;
wherein said beam delivery system is movable with respect to the treatment pod by at least one drive mechanism in order to adjust the position of said radiation beam with respect to said treatment room; and
wherein the system further includes a plurality of waiting rooms, said treatment pod being aligned with or movable together with the beam delivery system, into alignment with each of said waiting rooms to allow access to the treatment room from each waiting room via said first or second end.

21. A radiation therapy system comprising:

a treatment pod comprising a hollow body structure that defines an internal treatment room, the pod having first and second ends either one or both of which provides access to the treatment room; and a beam delivery system comprising a particle accelerator for generating a radiation beam;

wherein said beam delivery system is carried by said treatment pod and is configured to deliver said radiation beam to said treatment room;

wherein said beam delivery system is movable with respect to the treatment pod in order to adjust the position of said radiation beam with respect to said treatment room; and wherein the system further includes a plurality of waiting rooms, said treatment pod being aligned with or movable together with the beam delivery system, into alignment with each of said waiting rooms to allow access to the treatment room from each waiting room via said first or second end.

* * * * *